US006339113B1

(12) United States Patent
Han et al.

(10) Patent No.: US 6,339,113 B1
(45) Date of Patent: Jan. 15, 2002

(54) PHOTOPOLYMERIZABLE COMPOSITE RESIN COMPOSITIONS FOR DENTAL RESTORATION

(75) Inventors: Dong-Keun Han; Kwang-Duk Ahn; Jong-Man Kim; Jin-Hee Jeong, all of Seoul (KR)

(73) Assignee: Dentkist Co., Ltd., Seoul (KR)

( * ) Notice: Subject to any disclaimer, the term of this patent is extended or adjusted under 35 U.S.C. 154(b) by 0 days.

(21) Appl. No.: 09/698,037

(22) Filed: Oct. 30, 2000

(30) Foreign Application Priority Data

Jul. 5, 2000 (KR) .............................. 00-38132

(51) Int. Cl.$^7$ .................................................. C08F 2/46
(52) U.S. Cl. .......................... 522/100; 522/77; 522/83; 522/81; 522/79; 522/109; 522/111; 522/170; 522/182; 522/181; 522/908; 523/115; 523/116; 523/113; 523/111; 523/117; 523/118
(58) Field of Search ............................. 522/71, 77, 100, 522/83, 109, 9, 112, 8, 908, 79, 110, 28, 111, 14, 170, 169, 182, 81, 48; 523/111, 113, 115, 116, 117, 118

(56) References Cited

U.S. PATENT DOCUMENTS

| | | | |
|---|---|---|---|
| 3,066,112 A | 11/1962 | Bowen | |
| 3,730,947 A | 5/1973 | Stoffey et al. | |
| 4,102,856 A | 7/1978 | Lee, Jr. | |
| 4,131,729 A | 12/1978 | Schmitt et al. | |
| 4,381,918 A * | 5/1983 | Ehrnford | 433/199 |
| 4,491,453 A * | 1/1985 | Koblitz et al. | 433/217 |
| 4,540,723 A * | 9/1985 | Ying | 523/115 |
| 4,544,467 A * | 10/1985 | Bunker et al. | 204/159.24 |
| 4,669,983 A * | 6/1987 | Bunker et al. | 433/217.1 |
| 4,674,980 A * | 6/1987 | Ibsen et al. | 433/228.1 |
| 5,177,121 A * | 1/1993 | Bunker | 532/116 |
| 5,264,485 A * | 11/1993 | Muller et al. | 524/724 |
| 5,334,625 A * | 8/1994 | Ibsen et al. | 523/115 |
| 5,756,559 A * | 5/1998 | Blackwell et al. | 523/115 |
| 6,184,339 B1 * | 2/2001 | Stansbury et al. | 528/407 |

* cited by examiner

Primary Examiner—James J. Seidleck
Assistant Examiner—Sanza L. McClendon
(74) Attorney, Agent, or Firm—Oblon, Spivak, McClelland, Maier & Neustadt, P.C.

(57) ABSTRACT

The invention relates to a photopolymerizable composite resin composition for dental restoration i) based on the multifunctional prepolymer mixture of 2,2-bis-(4-(2-hydroxy-3-methacryloyloxypropoxy)phenyl)propane ("Bis-GMA") and multifunctional prepolymer formed by substituting hydrogen atoms in hydroxyl group with methacrylate groups in this Bis-GMA molecules, and ii) comprising a diluent, an inorganic filler, a photoinitiation system, and other additives. The photopolymerizable composite resin composition for dental restoration based on multifunctional prepolymer mixture has better physical and mechanical properties and biocompatibility than the conventional composition based on only Bis-GMA itself.

24 Claims, No Drawings

PHOTOPOLYMERIZABLE COMPOSITE RESIN COMPOSITIONS FOR DENTAL RESTORATION

BACKGROUND OF THE INVENTION

1. Field of the Invention

The present invention relates to photopolymerizable composite resin compositions for dental restoration having improved physical and mechanical properties, and biocompatibility, and long time sustainability after operation. More particularly, the invention relates to new photopolymerizable composite resin composition for dental restoration i) based on the multifunctional prepolymer mixture of 2,2-bis-(4-(2-hydroxy-3-methacryloyloxypropoxy) phenyl)propane ("Bis-GMA") and multifunctional prepolymer formed by substituting hydrogen atoms in hydroxyl group with methacrylate groups in the Bis-GMA molecules, and ii) comprising a diluent, an inorganic filler, a photoinitiation system, and other additives.

2. Description of the Prior Art

Polymethylmethacrylate (PMMA) is one example of a dental polymer material that is used as a denture base, an impression material, an adhesive, a dental restoration material and so on, of which the latter is most frequently used.

A mercury amalgam has been generally used as dental restoration materials up to date. It is reported that mercury amalgam can be easily applied, and that it has superior mechanical physical properties such as abrasion resistance and mechanical strength. But it is also a distinctly different color from that of natural teeth, and has poor adhesion with teeth tissues. In addition, it is reported that mercury amalgam is harmful to the human body due to the long term gradual outflow of mercury.

Accordingly, many recent studies have been conducted to develop materials to complement the defects of mercury amalgam or to substitute it for something else. Acrylic resins, which were first used as polymer material resins and have superior mechanical properties in terms of strength, color stability, and water-resistant stability when compared to silicates that have been developed since mercury amalgam are defective in that they have poor abrasion resistance and high shrinkage upon curing. In order to overcome these defects, high filling composite resins using inorganic fillers as reinforcement are developed as dental restoration materials.

A photopolymerizable composition for dental restoration is conventionally composed of an inorganic filler, a prepolymer, a diluent, a photoinitiation system (a photoinitiator and a reductant), and other additives and so on. The composition should meet the requirements of mechanical strength to support the high biting pressure generated when chewing food, the coefficient of heat expansion similar to the tooth, and a polymerization shrinkage low enough to inhibit exfoliation from tooth upon polymerization-curing. Together with its physical properties, the composition should also be the same color and gloss of the natural tooth, and provide a natural tongue-touch feeling of the restored tooth.

2,2-bis-(4-(2-hydroxy-3-methacryloyloxypropoxy) phenyl)propane (Bis-GMA), which is a dimethacrylate, is most generally used as a prepolymer of a photopolymerizable composition for dental restoration. The Bis-GMA is principally low in volatility and polymerization shrinkage. A polymer prepared from the Bis-GMA has the advantages of superior strength and, thus, the Bis-GMA is used as a matrix resin. U.S. Pat. No. 4,102,856, U.S. Pat. No. 4,131,729, and U.S. Pat. No. 3,730,947 and so on describes the use of the Bis-GMA. However, the Bis-GMA has high viscosity that requires the addition of a diluent such as triethylene glycol dimethacrylate (TEGDMA) since it is advantageous that a prepolymer such as the Bis-GMA should have low viscosity in order to be efficiently mixed with an inorganic filler. Also, moisture absorption due to hydroxyl group (—OH) in the molecular structure of the Bis-GMA makes the physical property or aesthetics of the cured substances impermanent.

The dental composite material includes a dental composite filling material for dental restoration to fill a cavity caused by dental caries, a crown material, a coalescence material, a dentition correction material, and an artificial tooth material. U.S. Pat. No. 3,066,112 describes various compositions for early dental composite resin, which have not been used in practice since there were various defects on restoring posterior teeth. An amalgam formed from a silver alloy and mercury has been in use from before 1900 as a dental restoring material, but it has been gradually substituted with a material of organic polymer due to its dangerous side effects to humans and circumstances.

The first dental composite resin was prepared by mixing the PMMA powder and a methylmethacrylate (MMA) monomer by Kulzer Corp. (Germany) in 1942 and has been clinically used. The acrylic resin has been used for a long time. However, an organic polymer has such advantages as aesthetics, operation simplicity, and low toxicity, but the polymer itself lacks such physical properties as hardness, strength, and abrasion resistance to support against chewing. Thus, a composite resin compounded with an inorganic filler was developed.

Brown developed a chemical initiating type of commercial composite resin in 1962. Due to the development in the 1970s of ultraviolet-photopolymerization and, subsequently, to the development in the 1980s of visible ray-photopolymerization by ICI (England), polymer composite materials have encroached on conventional amalgams, and their use has increased dramatically.

Dental restoration material is used in anterior filling, posterior filling, cervical erosion filling, fractured porcelain repair, bracket bonding, core building, anterior interdental diastasis treatment, discoloration- and coloration-tooth treatment, and porcelain laminate bonding and so on. In addition to the restoration of dental caries, this dental restoration material is applied in various kinds of dental treatment, such as bonding and coalescense, with an increasing demands for various kinds of aesthetic treatment.

This polymer composite resin has, thus, secured itself a position as a dental restoration material as a result of the above-mentioned uses. However, it still must be improved with respect to the strength, hardness, polymerization shrinkage, water absorption, and solubility, toxicity and aesthetics of the cured substance made of the material.

SUMMARY OF THE INVENTION

It is an object of the invention to provide a photopolymerizable composite resin composition for dental restoration having higher photocuring conversion, strength, and hardness as well as physical and mechanical properties such as low polymerization shrinkage and water absorption, and improved biocompatibility than the conventional composite resin composition for dental restoration.

Other objects and advantages of the invention will be clarified in the following detailed description of the invention.

DETAILED DESCRIPTION OF THE INVENTION

Hereinafter, the present invention is described in detail.

The object of the invention is achieved by means of a photopolymerizable composite resin composition for dental restoration that i) has improved physical and mechanical properties and biocompatibility;

ii) is based on the multifunctional prepolymer mixture of 2,2-bis-(4-(2-hydroxy-3-methacryloyloxypropoxy)phenyl)propane ("Bis-GMA") and at least one multifunctional prepolymer containing multimethacrylate groups formed by substituting hydrogen atoms in hydroxyl groups with methacrylate groups in the Bis-GMA molecules; and iii) comprises an adequate amount of a diluent, an inorganic filler, a photoinitiation system and other additives.

Generally, the Bis-GMA has been most frequently used as a prepolymer for dental restoration because of its superior physical properties, such as high strength after curing. The Bis-GMA molecule has two hydroxyl groups that play a role in promoting an affinity between an organic resin and an inorganic filler, whereas said hydroxyl groups have a property to absorb water due to its high hydrophilicity. In cases where an organic resin absorbs water, the physical properties and aesthetics of a photocured substance is gradually reduced. Thus, if a polymerized resin is swelled by water-absorption, the binding force between it and the filler is weakened so that the filler particle is likely to separate from the resin, thus weakening strength and abrasive resistance. In addition, cytotoxicity is caused, or food absorbs in the restored substance and becomes discolored.

The present inventors have conducted extensive research to improve the aforesaid problems of conventional photopolymerizable restoration material prepared by using only Bis-GMA prepolymer. We have found that a photopolymerizable composite resin composition for dental restoration can be prepared from a prepolymer mixture of Bis-GMA and trifunctional methacrylate prepolymer (Tri-GMA) and/or tetrafunctional methacrylate prepolymer (Tetra-GMA) having reduced hydrophilicity which is formed by substituting at least one hydrogen atoms in the two hydroxyl groups with methacrylate groups in the Bis-GMA molecule. We have also found that the polymerization shrinkage and water absorption that causes physical and mechanical properties and aesthetics deterioration of the resulting photocured substance can be reduced.

The first embodiment of the present invention provides a photopolymerizable composite resin composition for dental restoration comprising:

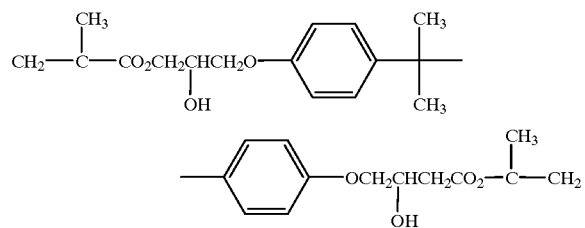

(A) 2 to 40 wt % of the prepolymer mixture comprising 2,2-bis-(4-(2-hydroxy-3-methacryloyloxypropoxy)phenyl)propane ("Bis-GMA") of formula 1:

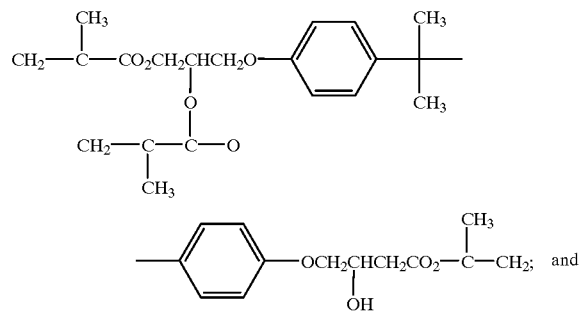

Tri-GMA of formula 2:

(B) 1 to 20 wt % of a diluent;

(C) 40 to 95 wt % of an inorganic filler;

(D) a photoinitiation system; and (E) other additives, wherein wt % of all the components are based on the total weight of the composition.

In accordance with the first embodiment, the weight ratio of Bis-GMA of formula 1 to Tri-GMA of formula 2 is 95:5 to 5:95.

The second embodiment of the present invention provides a photopolymerizable composite resin composition for dental restoration comprising:

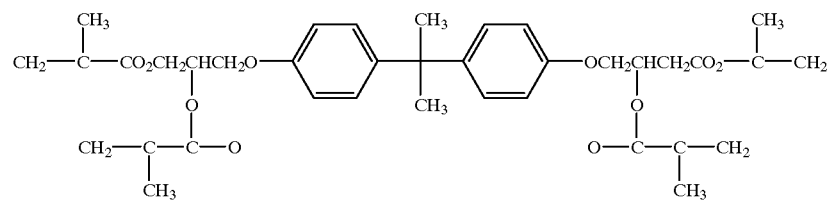

(A) 2 to 40 wt % of the prepolymer mixture comprising Bis-GMA of formula 1 and Tetra-GMA of formula 3:
(B) 1 to 20 wt % of a diluent;
(C) 40 to 95 wt % of an inorganic filler;
(D) a photoinitiation system; and
(E) other additives, wherein wt % of all the components are based on the total weight of the composition.

In accordance with the second embodiment, the weight ratio of Bis-GMA of formula 1 to Tetra-GMA of formula 3 is 95:5 to 5:95.

The third embodiment of the present invention provides a photopolymerizable composite resin composition for dental restoration comprising:

(A) 2 to 40 wt % of the prepolymer mixture of Bis-GMA of formula 1, Tri-GMA of formula 2, and Tetra-GMA of formula 3;
(B) 1 to 20 wt % of a diluent;
(C) 40 to 95 wt % of an inorganic filler;
(D) a photoinitiation system; and
(E) other additives,
wherein wt % of all the components are based on the total weight of the composition, and the prepolymer mixture consists of 90 to 5 wt % of Bis-GMA of formula 1, 90 to 5 wt % of Tri-GMA of formula 2, and 90 to 5 wt % of Tetra-GMA of formula 3.

In accordance with the photopolymerizable composite resin composition for dental restoration of the invention, Tri-GMA of formula 2 and Tetra-GMA of formula 3, constituting the prepolymer mixture, may be synthesized by substituting at least one hydrogen atoms in the two hydroxyl groups with methacrylate group in Bis-GMA molecules of formula 1. Thus, scheme 1 shows that Tri-GMA and Tetra-GMA may be quantitatively synthesized by reacting Bis-GMA with methacryol chloride in the presence of organic amine, for example triethylamine.

Scheme 1

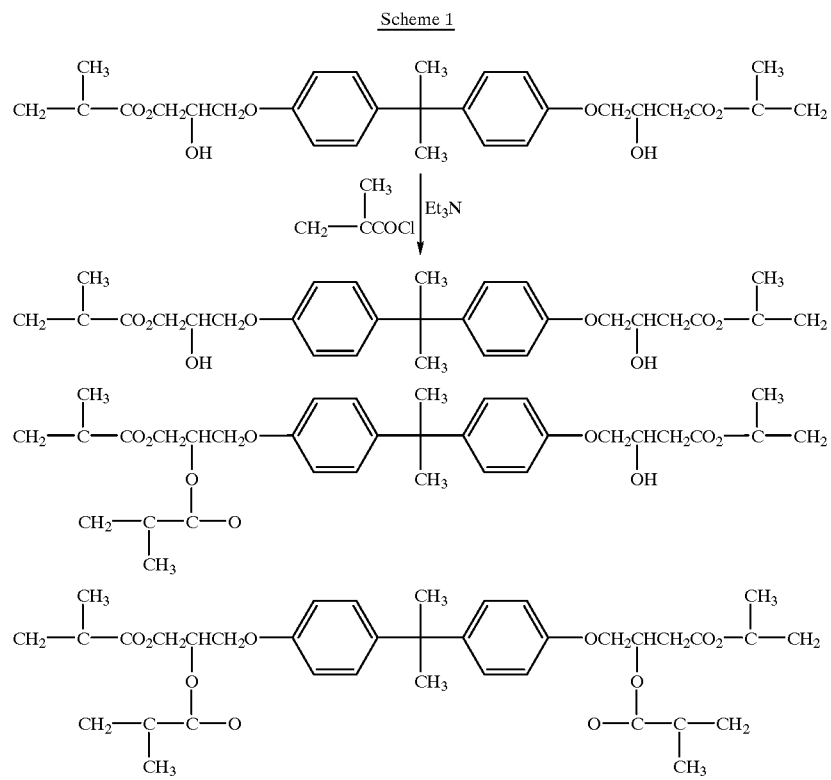

The synthesized multifunctional prepolymer mixture is separated into the individual of Bis-GMA, Tri-GMA, and Tetra-GMA through the column using a developer of mixture of ethyl acetate and n-hexane (50:50 weight ratio).

In accordance with the present invention, the photopolymerizable composite resin composition for dental restoration comprises a prepolymer mixture in an amount of 2 to 40 wt % based on the total weight of the composition.

In accordance with the present invention, the composition comprises a diluent to reduce the viscosity of the prepolymer mixture. The suitable examples of the diluent are methyl methacrylate, ethylene glycol dimethacrylate (EGDMA), diethylene glycol dimethacrylate (DEGDMA), triethylene glycol dimethacrylate (TEGDMA), 1,4-butanediol dimethacrylate, 1,6-hexanediol dimethacrylate, 1-methyl-1,3-propanediol dimethacrylate or 1,6-bis(methacryloloxy-2-ethoxycarbonylamino)-2,2,4-trimethylhexane. The composition comprises a diluent in an amount of 1 to 20 wt % based on the total weight of the composition.

In accordance with the present invention, the composition comprises an inorganic filler in order to improve the mechanical property of the composition and to make the composition opaque to X-ray. The inorganic filler is preferably quartz, barium glass, barium glass/silica, barium glass mixture, quartz/barium glass, silica, zirconia/silica, silica mixture, alumino silicate, lithium alumino silicate and barium aluminosilcate with a particle size of 0.005 to 20 μm, surface-treated with a silane coupling agent, and added in an amount of 40 to 95 wt % based on the total weight of the composition.

In order to surface-treat the inorganic filler, a silane coupling agent is primarily used. The representative examples are γ-methacryloxy propyl trimethoxysilane (γ-MPS), vinyl triethoxysilane, dimethyl dichlorosilane, hexamethylene disilizane, dimethyl polysiloxane and so on.

The composite resin composition for dental restoration of the present invention is exposed to visible rays that are unharmful to the human body so that a radical is formed from a photoinitiator and a catalyst. Said radical initiates polymerization of a monomer for curing the composition. Polymerization primarily occurs by exposure of the photo-initiator such as α-diketone aliphatic and aromatic carbonyl compound and tert-amine catalyst to the visible ray under a wavelength ranging from 400 to 500 nm. The photoinitiation system consists of a photoinitiator and a reductant. The photoinitiator is preferably camphorquinone (CQ), and added in an amount of 0.1 to 5 wt %. If CQ is photo excited to extract hydrogen in the reductant, the reductant practically initiates radical polymerization. A reductant such as N,N-dimethylaminoethyl methacrylate (DMAEMA) or ethyl p-dimethyl aminobenzoate (EDMAB) is added in an amount of 0.1 to 5 wt % based on the total weight of the composition.

Other additives such as a polymerization inhibitor, a lightstabilizer, an antioxidant, and a pigment to conform the color of the composite resin may be added. A polymerization inhibitor such as hydroquinone (HQ), hydroquinone monomethyl ether or hydroquinone monoethyl ether may be added in an amount of 0.1 to 10 wt % based on the total weight of the composition. A lightstabilizer such as Tinubin may be added in an amount of 0.01 to 5 wt % based on the total weight of the composition. An antioxidant such as Iganox and 2,6-di-tert-butyl-4-methyl phenol butylated hydroxytoluene (BHT) may be added in an amount of 0.01 to 5 wt % based on the total weight of the composition. Inorganic pigments of yellow, navy blue, or red colored-iron oxides and titanium dioxide may be added in an amount of 0.005 to 0.5 wt % based on the total weight of the composition.

The physical properties of the specimen from the resulting composition for dental restoration are estimated as follows:

1) Photoconversion

A photopolymerization efficiency caused by the visible ray is estimated by means of infrared absorption spectroscopy. The conversion of the methacrylate monomer is calculated by measuring the decreased area of the absorption band at 1638 cm$^{-1}$ by the aliphatic double bond on the basis of the area of the absorption band at 1609 cm$^{-1}$ by the aromatic ring.

2) Polymerization Depth

A 4 mm (diameter)×10 mm (height) metal mold is placed on a transparent film covered with a white paper filter and subsequently filled with a restoring material free of air bubbles. A transparent film is then placed on the top of the mold, and excessive material is removed by pressurization. By photo irradiation, the polymerization depth in accordance with the exposure time is measured to an accuracy of 0.01 mm with a micrometer.

3) Polymerization Shrinkage

A cylinder shaped specimen (6.0×3.3 mm) is placed in a transparent glass mold, and cured with a light-irradiator. Density of the specimen is measured with a picnometer before and after curing the specimen, and calculated according to the following formula.

$$\text{Polymerization shrinkage}(\%) = \left(1 - \frac{d\text{uncured}}{d\text{cured}}\right) \times 100$$

4) Water Absorption and Solubility

A composite resin composition is made into about a 6 cm (diameter)×3 mm (height) specimen, which is cured. The weight of the cured specimen is measured, and then the cured specimen is dipped into distilled water at 37° C. After every 24 or 48 hours, the specimen is then taken out, water is removed from the specimen, and the weight of the specimen is measured. Moisture absorption is calculated by the following formula.

$$\text{Water absorption}(\%) = \left(\frac{\text{weight after dipping} - \text{weight after cure before dipping}}{\text{weight after cure before dipping}}\right) \times 100$$

In order to measure solubility, the specimen is taken out, and the water is removed from the specimen. The specimen is completely dried again in a desiccator to have uniform weight, and the weight of the specimen is measured. Solubility is calculated by the following formula.

$$\text{Solubility}(\%) = \left(\frac{\text{weight after cure before dipping} - \text{weight after dipping and complete drying}}{\text{weight after cure before dipping}}\right) \times 100$$

5) Radio-opacity

Specimen (13 mm [diameter]×2 mm [thickness]) is prepared, and is placed together with an aluminium step-panel (purity: 99.9%, thickness: 2 mm) on X-ray film and radiated for 0.5 sec in 65±5 kvp and 15 mA, developed, and measured with a densitometer, and compared with the step-panel.

6) Diametral Tensile Strength

The diametral tensile strength measurement method, in which stable compression stress is applied to a specimen instead of direct tensile strength, is used especially in the measurement of the physical properties of dental material. In this method, a disk shaped specimen is laid horizontally, and compression weight is applied to the specimen to cause tensile stress interior of the specimen. A 6 mm (diameter)× 3.6 mm (thickness) specimen is prepared, and stress is applied to the specimen in cross-head speed of 0.5±0.2 mm/sec with a tensile tester until the specimen is fractured. The diametral tensile strength is calculated by the following formula.

$$\text{Diametral tensile strength}(DTS) = \frac{2 \times \text{maximum load}}{\pi \times \text{diameter of specimen} \times \text{thickness of specimen}}$$

7) Flexural Strength

Photo irradiation is conducted on both sides of a mold (25 mm×2 mm×2 mm) to produce a specimen, which is kept in distilled water at 37° C. for 24 hours. Stress is applied to the specimen in cross-head speed of 0.75±0.25 mm/sec with tensile tester until the specimen is fractured. The flexural strength is calculated by the following formula.

$$\sigma = \frac{3 \times \text{maximumload} \times \text{distance between supporters}}{2 \times \text{area of specimen} \times \text{height of specimen}}$$

8) Cytotoxicity

Cytotoxicity of a composite resin is estimated by comparing the toxicity degree according to the agar layered plate method. 10 mm (diameter)×2 mm (thickness) specimen is tested using polyvinylchloride [PVC, response rate: 3/4] as the positive control group and polyethylene (PE) as the negative control group. The specimen is first adhered to an L-929 cell suspension using Eagle's agar medium, and incubated for 24 hours at a temperature of 37° C. in a 5% $CO_2$ incubator. The cell lysis ratio is measured in a discolored region of the specimen and is indicated as a zone index and lysis index, as listed in Table 1, from which a response index (RI=zone index/lysis index) is calculated. Cytotoxicity is evaluated from RI as it is listed in Table 2. The lower the value, the lower the toxicity.

TABLE 1

Definition of each index value

| Index | Definition |
| --- | --- |
| Zone Index | Discolored area |
| 0 | None is permeated under the specimen |
| 1 | The limited area under the specimen |
| 2 | Area diffused from sample <0.5 cm |
| 3 | Area diffused from sample <1 cm |
| 4 | Area diffused from sample ≧1 cm, <total area |
| 5 | Area diffused from sample : total area |
| Lysis Index | Lysis area |
| 0 | None |
| 1 | <20% |
| 2 | 20–40% |
| 3 | 40–60% |
| 4 | 60–80% |
| 5 | ≧80% |

TABLE 1

Evaluation of cytotoxicity

| Scale | RI | Cytotoxicity |
| --- | --- | --- |
| 0 | 0/0 | none |
| 1 | 1/1 | weak |
| 2 | 2/2 to 3/3 | medium |
| 3 | 4/4 to 5/5 | severity |

Hereinafter, the present invention is illustrated in detail by the examples given below. However, the examples are presented here only for illustrative purposes and should not be construed as limiting the invention.

EXAMPLE 1

Preparation of Multifunctional Prepolymer

Bis-GMA (51.2 g, 0.1 mol) was dissolved in methylene chloride (50 ml) and, subsequently, 10.2 g of triethylamine (0.1 mol) was added. Methacryloyl chloride (7.9 g, 0.75 mol) was slowly added while the solution was stirred in an ice bath. The solution was stirred at room temperature and precipitated salt was then filtered out and removed. A filtrate was washed with distilled water, dehydrated, and distilled under reduced pressure to quantitatively obtain a viscous liquid. The result of the component ratio of the obtained multifunctional prepolymer mixture showed that Bis-GMA of formula 1, Tri-GMA of formula 2, and Tetra-GMA of formula 3 were obtained with respective weight ratios of 45:45:10.

The result of infrared spectroscopy showed that the absorption band at 939 and 1638 $cm^{-1}$ by a double bond as well as almost all absorption bands, are coincident with the absorption band of Bis-GMA, whereas the absorption band (3400 $cm^{-1}$) caused by the hydroxyl group was greatly decreased.

EXAMPLE 2

Preparation of Composition Based on 50:50 wt % Prepolymer Mixture of Bis-GMA and Tri-GMA Multifunctional prepolymer prepared in Example 1 was separated to Bis-GMA, Tri-GMA, and Tetra-GMA, respectively, through the use of a column. The separated Tri-GMA and the existing Bis-GMA were mixed at 50:50 wt %. Bis-GMA (4.7 wt %) and 4.7 wt % of Tri-GMA were used as a prepolymer, and 4 wt % of TEGDMA, 80 wt % of barium glass, 1 wt % of CQ, 2 wt % of EDMAB, 3 wt % of HQ, 0.5 wt % of Tinubin, 0.1 wt % of Iganox, and a small amount of inorganic pigment based on the total weight of the composition were added thereto.

With respect to this adding procedure, the diluent, the inorganic filler, and the polymerization inhibitor were first added to the prepolymer mixture and mixed to uniformly disperse a large quantity of the inorganic filler and, subsequently, the photoinitiator, the reductant, and other additives were added and uniformly dispersed to prepare a photopolymerizable composite resin composition for dental restoration.

EXAMPLE 3

Preparation of Composition Based on 45:45:10 wt % Prepolymer Mixture of Bis-GMA, Tri-GMA and Tetra-GMA The prepolymer mixture (10.4 wt %), 4 wt % of EGDMA, 80 wt % of silica, 1 wt % of CQ, 1 wt % of DMAEMA, 3 wt % of HQ, 0.5 wt % of Tinubin, 0.1 wt % of Iganox, and a small amount of inorganic pigment based on the total weight of the composition were added in the procedure described in example 2 to prepare a photopolymerizable composite resin composition for dental restoration.

EXAMPLE 4

Preparation of Composition Based on 75:25 wt % Prepolymer Mixture of Bis-GMA and Tri-GMA Bis-GMA (6.5 wt %), 2.2 wt % of Tri-GMA, 4.7 wt % of DEGDMA, 1 wt % of CQ, 2 wt % of EDMAB, 3 wt % of HQ monomethyl ether, 80 wt % of barium glass/silica, 0.5 wt % of Tinubin, 0.1 wt % of BHT, and a small amount of inorganic pigment based on the total weight of the composition were added in the procedure described in example 2 to prepare a photopolymerizable composite resin composition for dental restoration.

EXAMPLE 5

Preparation of Composition Based on 25:75 wt % Prepolymer Mixture of Bis-GMA and Tri-GMA Bis-GMA (2.5 wt %), 7.5 wt % of Tri-GMA, 3.4 wt % of TEGDMA, 1 wt % of CQ, 2 wt % of DMAEMA, 3 wt % of HQ monoethyl ether, 80 wt % of barium glass, 0.5 wt % of Tinubin, 0.1 wt % of Iganox, and a small amount of inorganic pigment based on the total weight of the composition were added in the procedure described in example 2 to prepare a photopolymerizable composite resin composition for dental restoration.

EXAMPLE 6

Preparation of Composition Based on 50:50 wt % Prepolymer Mixture of Bis-GMA and Tetra-GMA Bis-GMA (4.7 wt %) and 4.7 wt % of Tetra-GMA that is used as prepolymer mixture, 4 wt % of TEGDMA, 80 wt % of barium glass, 1wt % of CQ, 2 wt % of EDMAB, 3 wt % of HQ, 0.5 wt % of Tinubin, 0.1 wt % of Iganox, and a small amount of inorganic pigment based on the total weight of the composition were added in the procedure described in example 2 to prepare a photopolymerizable composite resin composition for dental restoration.

COMPARATIVE EXAMPLE 1

Preparation of Composition Based on Only Bis-GMA Prepolymer Itself

Bis-GMA (9.0 wt %), 5.4 wt % of TEGDMA, 80 wt % of barium glass, 1wt % of EDMAB, 3 wt % of HQ, 0.5 wt % of Tinubin, 0.1 wt % of Iganox, and a small amount of inorganic pigment based on the total weight of the composition were added in the procedure described in example 2 to prepare a photopolymerizable composite resin composition for dental restoration.

COMPARATIVE EXAMPLE 2

Preparation of Composition Based on Only Tri-GMA Prepolymer Itself

Tri-GMA (10.7 wt %), 2.7 wt % of TEGDMA, 80 wt % of silica, 1 wt % of CQ, 2% of DMAEMA, 3% of HQ, 0.5 wt % of Tinubin, 0.1% of Iganox, and a small amount of inorganic pigment based on the total weight of the composition were added in the procedure described in example 2 to prepare a photopolymerizable composite resin composition for dental restoration.

Table 3 shows the estimated results of the physical properties of the composition prepared in the examples and comparative examples.

TABLE 3

Physical property estimated result

| Physical property factor | Example | | | | | Comparative example | |
|---|---|---|---|---|---|---|---|
| | 2 | 3 | 4 | 5 | 6 | 1 | 2 |
| Photoconversion (%) | 50 | 50 | 48 | 47 | 48 | 45 | 40 |
| Polymerization depth (mm) | 9.9 | 9.8 | 9.7 | 9.8 | 9.8 | 9.2 | 9.0 |
| Polymerization shrinkage (%) | 2.1 | 2.0 | 3.1 | 3.3 | 2.0 | 6.5 | 4.0 |
| Water absorption (%) | 15 | 14 | 18 | 14 | 14 | 20 | 13 |
| Solubility ($\mu g/mm^3$) | 1.2 | 1.1 | 2.0 | 1.1 | 1.1 | 2.4 | 1.0 |
| Radio-opacity | 0.33 | 0.32 | 0.30 | 0.30 | 0.30 | 0.28 | 0.31 |
| Diametral tensile strength (MPa) | 45 | 45 | 43 | 43 | 43 | 40 | 40 |
| Flexural strength (MPa) | 136 | 137 | 131 | 130 | 134 | 117 | 118 |
| Cytotoxicity (RI) | 0/1 | 0/1 | 1/1 | 1/1 | 0/1 | 1/1 | 1/1 |

According to the present invention, Bis-GMA and Tri-GMA and/or Tetra-GMA prepolymer mixture can reduce polymerization shrinkage and water absorption due to blocking hydroxyl group in comparison with Bis-GMA, which is itself a prepolymer. Also, the prepolymer mixture has very low viscosity so that the diluent may be added in a small amount, and the inorganic filler which most greatly affects the strength of restoration substances may be compounded in a greater amount. Accordingly, the physical properties of the restoration substance are enhanced.

The photopolymerizable composite resin composition for dental restoration in accordance with the present invention has good physical and mechanical properties, such as photoconversion, polymerization depth, polymerization shrinkage, water absorption and solubility, radio-opacity, diametral tensile strength and flexural strength, and enhanced cytotoxicity. Especially, the composite resin composition for dental restoration based on the 50:50 wt % mixture of Bis-GMA and Tri-GMA offers the best physical and mechanical properties and improved biocompatibility to provide a photopolymerizable composition for dental restoration for treating dental caries and so on.

What is claimed is:
1. A photopolymerizable composite resin composition for dental restoration comprising:

(A) 2 to 40 wt % of a prepolymer mixture comprising:

(i) 5 to 95 wt % 2,2-bis-(4-(2-hydroxy-3-methacryloyloxypropoxy)phenyl)propane ("Bis-GMA") of formula 1:

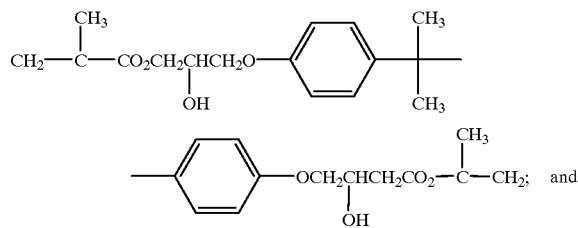

(ii) 95 to 5 wt % Tri-GMA of formula 2:

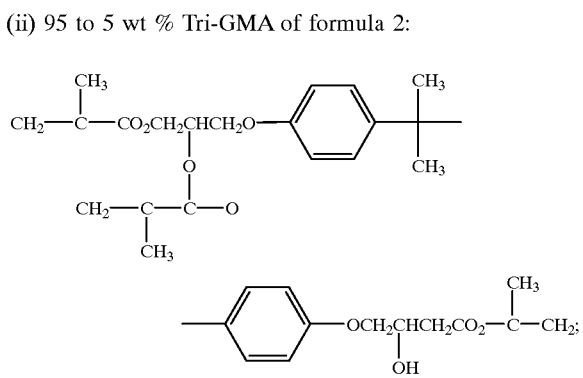

(B) 1 to 20 wt % of a diluent;
(C) 40 to 95 wt % of an inorganic filler;
(D) a photoinitiation system; and
(E) other additives,
 wherein wt % of all the components are based on the total weight of the composition.

2. A photopolymerizable composite resin composition for dental restoration comprising:

(A) 2 to 40 wt % of a prepolymer mixture comprising:

(i) 5 to 95 wt % 2,2-bis-(4-(2-hydroxy-3-methacryloyloxypropoxy)phenyl)propane ("Bis-GMA") of formula 1:

(ii) 95 to 5 wt % Tetra-GMA of formula 3:

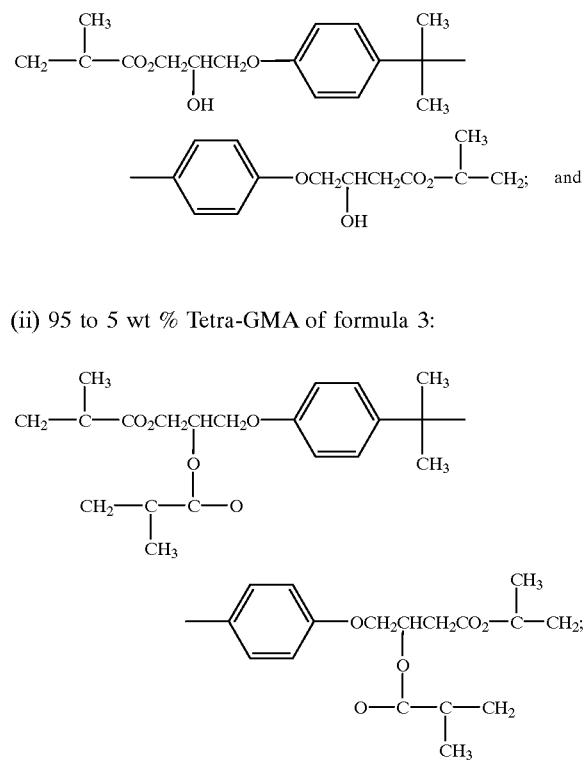

(B) 1 to 20 wt % of a diluent;
(C) 40 to 95 wt % of an inorganic filler;
(D) a photoinitiation system; and
(E) other additives,
 wherein wt % of all the components are based on the total weight of the composition.

3. A photopolymerizable composite resin composition for dental restoration comprising:

(A) 2 to 40 wt % of a prepolymer mixture comprising:

(i) 90 to 5 wt % 2,2-bis-(4-(2-hydroxy-3-methacryloyloxypropoxy)phenyl)propane ("Bis-GMA") of formula 1:

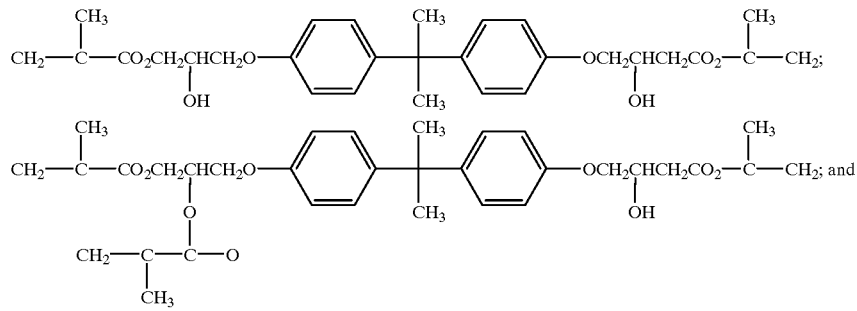

(iii) 90 to 5 wt % Tetra-GMA of formula 3:

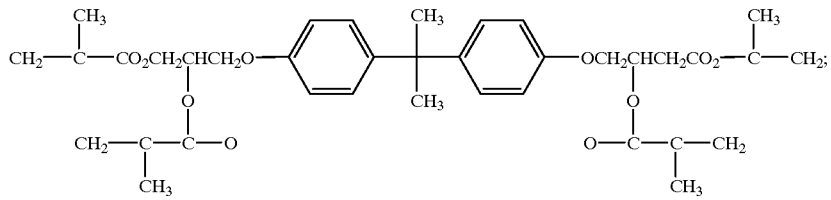

(B) 1 to 20 wt % of a diluent;
(C) 40 to 95 wt % of an inorganic filler;
(D) a photoinitiation system; and
(E) other additives,
wherein wt % of all the components are based on the total weight of the composition.

4. The photopolymerizable composite resin composition for dental restoration according to claim 1 wherein the diluent is selected from the group consisting of: methyl methacrylate, ethylene glycol dimethacrylate (EGDMA), diethylene glycol dimethacrylate (DEGDMA), triethylene glycol dimethacrylate (TEGDMA), 1,4-butanediol dimethacrylate, 1,6-hexane diol dimethacrylate, 1-methyl-1,3-propanediol dimethacrylate, and 1,6-bis(methacryloyloxy-2-ethoxycarbonylamino)-2,2,4-trimethylhexane.

5. The photopolymerizable composite resin composition for dental restoration according to claim 2 wherein the diluent is selected from the group consisting of: methyl methacrylate, ethylene glycol dimethacrylate (EGDMA), diethylene glycol dimethacrylate (DEGDMA), triethylene glycol dimethacrylate (TEGDMA), 1,4-butanediol dimethacrylate, 1,6-hexane diol dimethacrylate, 1-methyl-1,3-propanediol dimethacrylate, and 1,6-bis(methacryloyloxy-2-ethoxycarbonylamino)-2,2,4-trimethylhexane.

6. The photopolymerizable composite resin composition for dental restoration according to claim 3 wherein the diluent is selected from the group consisting of: methyl methacrylate, ethylene glycol dimethacrylate (EGDMA), diethylene glycol dimethacrylate (DEGDMA), triethylene glycol dimethacrylate (TEGDMA), 1,4-butanediol dimethacrylate, 1,6-hexane diol dimethacrylate, 1-methyl-1,3-propanediol dimethacrylate, and 1,6-bis(methacryloyloxy-2-ethoxycarbonylamino)-2,2,4-trimethylhexane.

7. The photopolymerizable composite resin composition for dental restoration according to claim 1 wherein the inorganic filler is selected from the group consisting of: quartz, barium glass, barium glass/silica, barium glass mixture, quartz/barium glass, silica, zirconia/silica, silica mixture, alumino silicate, lithium alumino silicate and barium aluminosilcate of particle size of 0.005 to 20 μm surface-treated with silane.

8. The photopolymerizable composite resin composition for dental restoration according to claim 2 wherein the inorganic filler is selected from the group consisting of: quartz, barium glass, barium glass/silica, barium glass mixture, quartz/barium glass, silica, zirconia/silica, silica mixture, alumino silicate, lithium alumino silicate and barium aluminosilcate of particle size of 0.005 to 20 μm surface-treated with silane.

9. The photopolymerizable composite resin composition for dental restoration according to claim 3 wherein the inorganic filler is selected from the group consisting of: quartz, barium glass, barium glass/silica, barium glass mixture, quartz/barium glass, silica, zirconia/silica, silica mixture, alumino silicate, lithium alumino silicate and barium aluminosilcate of particle size of 0.005 to 20 μm surface-treated with silane.

10. The photopolymerizable composite resin composition for dental restoration according to claim 7 wherein the silane for surface treatment of inorganic filler is selected from the group consisting of: trimethoxysilylpropylmethacrylate (γ-MPS), vinyl triethoxy silane, dimethyl dichloro silane, hexamethylene disilazane, and dimethyl polysiloxane.

11. The photopolymerizable composite resin composition for dental restoration according to claim 8 wherein the silane for surface treatment of inorganic filler is selected from the group consisting of: trimethoxysilylpropylmethacrylate (γ-MPS), vinyl triethoxy silane, dimethyl dichloro silane, hexamethylene disilazane, and dimethyl polysiloxane.

12. The photopolymerizable composite resin composition for dental restoration according to claim 9 wherein the silane for surface treatment of inorganic filler is selected from the group consisting of: trimethoxysilylpropylmethacrylate (γ-MPS), vinyl triethoxy silane, dimethyl dichloro silane, hexamethylene disilazane, and dimethyl polysiloxane.

13. The photopolymerizable composite resin composition for dental restoration according to claim 1 wherein the photoinitiation system comprises 0.1 to 5 wt % of a photoinitiator and 0.1 to 5 wt % of a reductant based on the total weight of the composition.

14. The photopolymerizable composite resin composition for dental restoration according to claim 2 wherein the photoinitiation system comprises 0.1 to 5 wt % of a photoinitiator and 0.1 to 5 wt % of a reductant based on the total weight of the composition.

15. The photopolymerizable composite resin composition for dental restoration according to claim 3 wherein the photoinitiation system comprises 0.1 to 5 wt % of a photoinitiator and 0.1 to 5 wt % of a reductant based on the total weight of the composition.

16. The photopolymerizable composite resin composition for dental restoration according to claim 13 wherein the photoinitiatior is camphoquinone, and the reductant is N,N-dimethylaminoethyl methacrylate or ethyl p-dimethyl aminobenzoate.

17. The photopolymerizable composite resin composition for dental restoration according to claim 14 wherein the photoinitiatior is camphoquinone, and the reductant is N,N-dimethylaminoethyl methacrylate or ethyl p-dimethyl aminobenzoate.

18. The photopolymerizable composite resin composition for dental restoration according to claim 15 wherein the photoinitiatior is camphoquinone, and the reductant is N,N-dimethylaminoethyl methacrylate or ethyl p-dimethyl aminobenzoate.

19. The photopolymerizable composite resin composition for dental restoration according claim 1 wherein the other additives comprises 0.5 to 10 wt % of a polymerization inhibitor, 0.01 to 5 wt % of a lightstabilizer, 0.01 to 5 wt % of an antioxidant and 0.005 to 0.5 wt % of a pigment based on the total weight of the composition.

20. The photopolymerizable composite resin composition for dental restoration according claim 2 wherein the other additives comprises 0.5 to 10 wt % of a polymerization inhibitor, 0.01 to 5 wt % of a lightstabilizer, 0.01 to 5 wt % of an antioxidant stabilizer and 0.005 to 0.5 wt % of a pigment based on the total weight of the composition.

21. The photopolymerizable composite resin composition for dental restoration according claim 3 wherein the other additives comprises 0.5 to 10 wt % of a polymerization inhibitor, 0.01 to 5 wt % of a lightstabilizer, 0.01 to 5 wt % of an antioxidant and 0.005 to 0.5 wt % of a pigment based on the total weight of the composition.

22. The photopolymerizable composite resin composition for dental restoration according to claim 19 wherein the polymerization inhibitor is selected from the group consisting of hydroquinone, hydroquinone monomethyl ether and hydroquinone monoethyl ether; the lightstabilizer is Tinubin; the antioxidant is Iganox or 2,6-di-tert-butyl-4-methylphenol butylated hydroxy toluene (BHT); and the pigment is iron oxides or titanium dioxide inorganic pigment.

23. The photopolymerizable composite resin composition for dental restoration according to claim 20 wherein the polymerization inhibitor is selected from the group consisting of hydroquinone, hydroquinone monomethyl ether and hydroquinone monoethyl ether; the lightstabilizer is Tinubin; the antioxidant is Iganox or 2,6-di-tert-butyl-4-methylphenol butylated hydroxy toluene (BHT); and the pigment is iron oxides or titanium dioxide inorganic pigment.

24. The photopolymerizable composite resin composition for dental restoration according to claim 21 wherein the polymerization inhibitor is selected from the group consisting of hydroquinone, hydroquinone monomethyl ether and hydroquinone monoethyl ether; the lightstabilizer is Tinubin; the antioxidant is Iganox or 2,6-di-tert-butyl-4-methylphenol butylated hydroxy toluene (BHT); and the pigment is iron oxides or titanium dioxide inorganic pigment.

* * * * *

UNITED STATES PATENT AND TRADEMARK OFFICE
CERTIFICATE OF CORRECTION

PATENT NO. : 6,339,113 B1  Page 1 of 1
DATED : January 15, 2002
INVENTOR(S) : Han et al.

It is certified that error appears in the above-identified patent and that said Letters Patent is hereby corrected as shown below:

<u>Title page,</u>
Item [73], Assignee, should read:
-- [73]   Assignees:   Korea Institute of Science and Technology, Seoul (KR); Dentkist Co., Ltd., Seoul (KR) --

Signed and Sealed this

Second Day of September, 2003

JAMES E. ROGAN
*Director of the United States Patent and Trademark Office*